(12) United States Patent
Cao Minh

(10) Patent No.: US 7,924,001 B2
(45) Date of Patent: Apr. 12, 2011

(54) DETERMINATION OF OIL VISCOSITY AND CONTINUOUS GAS OIL RATIO FROM NUCLEAR MAGNETIC RESONANCE LOGS

(75) Inventor: Chanh Cao Minh, Katy, TX (US)

(73) Assignee: Schlumberger Technology Corp., Sugar land, TX (US)

( * ) Notice: Subject to any disclaimer, the term of this patent is extended or adjusted under 35 U.S.C. 154(b) by 196 days.

(21) Appl. No.: 12/423,469

(22) Filed: Apr. 14, 2009

(65) Prior Publication Data
US 2009/0289628 A1 Nov. 26, 2009

Related U.S. Application Data

(60) Provisional application No. 61/055,943, filed on May 23, 2008.

(51) Int. Cl.
*G01V 3/00* (2006.01)
(52) U.S. Cl. ......................... 324/303; 324/306
(58) Field of Classification Search .................. 324/303, 324/306
See application file for complete search history.

(56) References Cited

U.S. PATENT DOCUMENTS

| | | | |
|---|---|---|---|
| 3,597,681 A | 8/1971 | Huckabay | |
| 4,710,713 A | 12/1987 | Strikman | |
| 5,055,788 A | 10/1991 | Kleinberg | |
| 5,992,519 A | 11/1999 | Ramakrishnan et al. | |
| 6,032,101 A * | 2/2000 | Freedman et al. | 702/8 |
| 6,107,796 A | 8/2000 | Prammer | |
| 6,111,408 A | 8/2000 | Blades | |
| 6,229,308 B1 * | 5/2001 | Freedman | 324/303 |
| 6,313,837 B1 | 11/2001 | Assa | |
| 6,346,813 B1 | 2/2002 | Kleinberg | |
| 6,825,657 B2 * | 11/2004 | Kleinberg et al. | 324/303 |
| 7,176,682 B2 * | 2/2007 | Galford et al. | 324/303 |
| 7,248,259 B2 | 7/2007 | Fremming | |
| 7,768,260 B2 * | 8/2010 | Chen et al. | 324/303 |
| 2003/0216897 A1 | 11/2003 | Endres | |
| 2004/0169511 A1 | 9/2004 | Minh | |
| 2005/0149307 A1 | 7/2005 | Gurpinar | |
| 2006/0197759 A1 | 9/2006 | Fremming | |

FOREIGN PATENT DOCUMENTS

| | | |
|---|---|---|
| WO | 9964896 | 12/1999 |
| WO | 2004049216 | 6/2004 |

OTHER PUBLICATIONS

Freedman et al., "A New NMR Method of Fluid Characterization in Reservoir Rocks: Experimental Confirmation and Simulation Results", SPE 75325, 2001.

(Continued)

*Primary Examiner* — Louis M Arana

(57) ABSTRACT

A method for determining oil viscosity and continuous gas-oil-ratio (GOR) from nuclear magnetic resonance logs (NMR). The method includes obtaining a set of NMR data of a portion of the subterranean formation from inside the wellbore without acquiring formation fluid sample; isolating a quantitative reservoir fluid information associated with oil from oil based mud (OBM) using radial profiling of the set of NMR data, wherein the OBM is used for extracting fluid from the underground reservoir; determining GOR related information associated with the portion of the subterranean formation from the quantitative reservoir fluid information associated with oil, wherein the GOR related information is determined based on a predetermined model; and performing operations for the oilfield based on the GOR related information.

15 Claims, 12 Drawing Sheets

OTHER PUBLICATIONS

Hirasaki et al., "NMR Proprties of Reservoir Fluids", AAPG, 2002.
Cao Minh, et al., "Planning and Interpreting NMR Fluid-Characterization Logs", SPE 84478, 2003.
Depavia, et al., "A Next-Generation Wireline NMR Logging Tool", SPE 8442, 2003.
Heaton, et al., "Saturation and Viscosity From Multidimensional Nuclear Resonance Logging", SPE 90564, 2004.

* cited by examiner

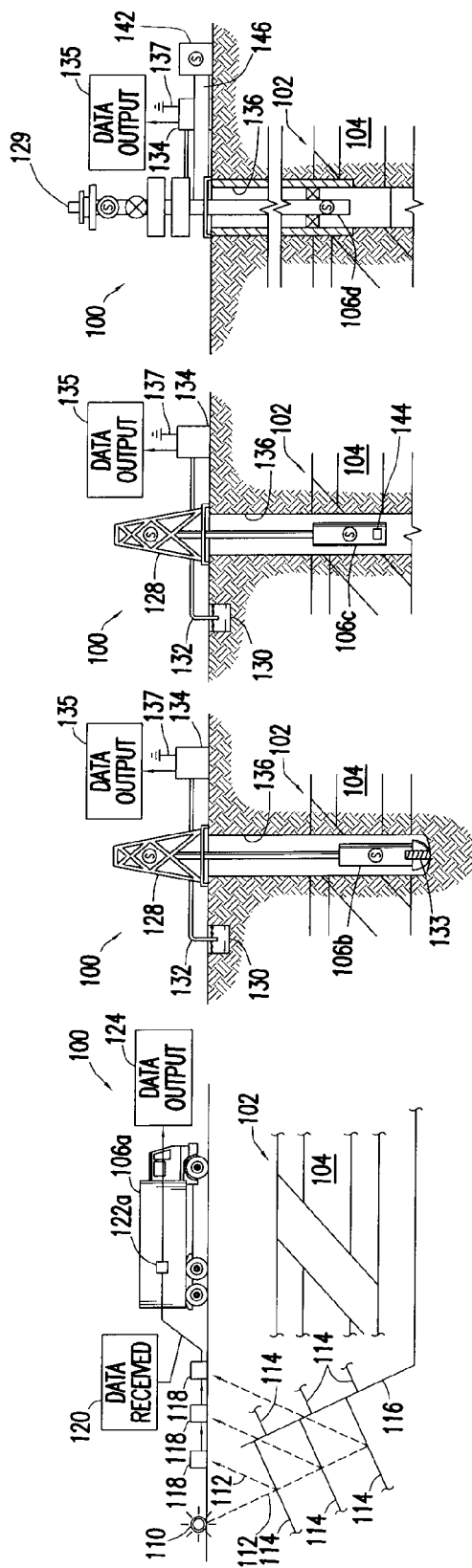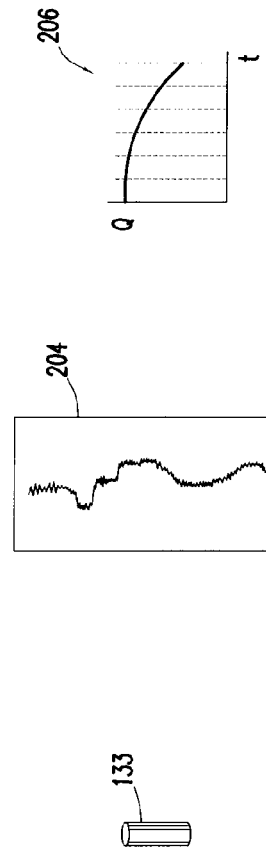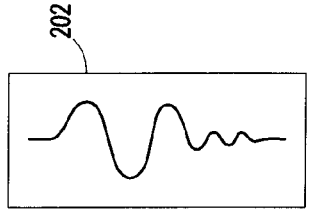

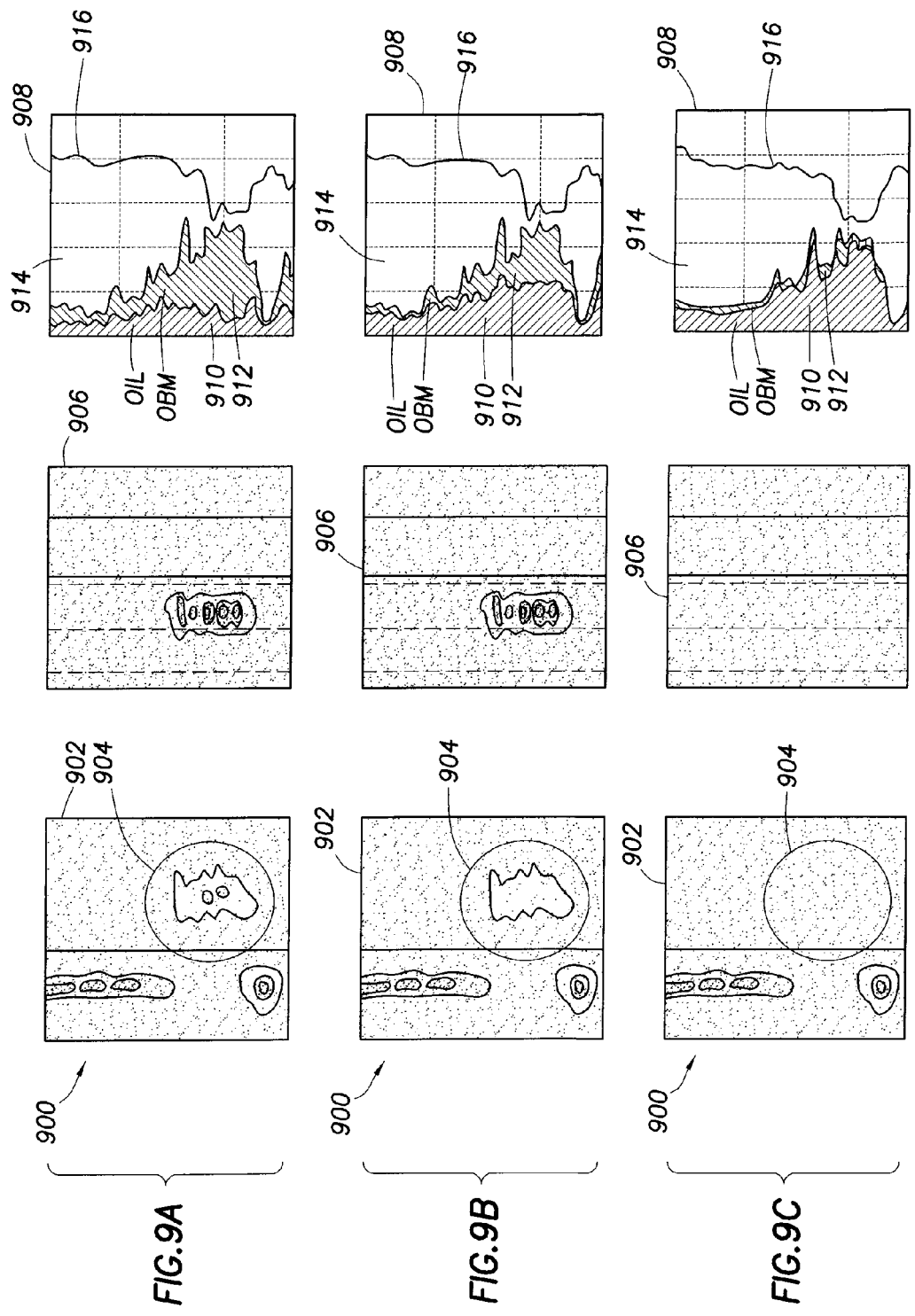

US 7,924,001 B2

DETERMINATION OF OIL VISCOSITY AND CONTINUOUS GAS OIL RATIO FROM NUCLEAR MAGNETIC RESONANCE LOGS

CROSS REFERENCE TO RELATED APPLICATIONS

This application claims priority under 35 U.S.C. §119(e) from Provisional Patent Application No. 61/055,943 filed May 23, 2008, entitled "System and Method for Determining Oil Viscosity and Continuous Gas Oil Ratio from Nuclear Magnetic Resonance Logs", which is hereby incorporated by reference in its entirety.

BACKGROUND

1. Field of the Invention

The present invention relates to techniques for determining formation fluid properties. More particularly, the invention relates to determination of the oil viscosity and continuous gas oil ratio (GOR) from nuclear magnetic resonance (NMR) logs.

2. Background of the Related Art

The oil and gas industry has developed various tools capable of determining formation fluid properties. For example, borehole fluid sampling and testing tools such as Schlumberger's Modular Formation Dynamics Testing (MDT™) Tool can provide important information on the type and properties of reservoir fluids in addition to providing measurements of reservoir pressure, permeability, and mobility.

These various tools may perform measurements of the fluid properties downhole, using sensor modules on board the tools. Alternatively, these tools can withdraw fluid samples from the reservoir that can be collected in bottles and brought to the surface for analysis. The collected samples are routinely sent to fluid properties laboratories for analysis of physical properties that include, among other things, oil viscosity, GOR, mass density or American Petroleum Institute (API) gravity, molecular composition, $H_2S$ (hydrogen sulfide), asphaltenes, resins, and various other impurity concentrations. However, the laboratory data may not be useful or relevant because it is discrete (non-continuous) and receiving the data after analysis is too late for real-time decision-making at the wellsite.

Techniques have been developed in analyzing formation fluid properties using NMR data. For example, SPE 75325 paper "A New NMR Method of Fluid Characterization in Reservoir Rocks: Experimental Confirmation and Simulation Results" by Freedman et al. presents techniques to evaluate water, oil, and gas in reservoirs; the paper "NMR Properties of Reservoir Fluids" by Hirasaki et al., published in AAPG 2002, describes GOR calculation from crude oil NMR data; SPE 84478 paper "Planning and Interpreting NMR Fluid-Characterization Logs" by Cao Minh et al., SPE 84482 paper "A Next-Generation Wireline NMR Logging Tool" by Depavia et al., and SPE 90564 paper "Saturation and Viscosity From Multidimensional Nuclear Magnetic Resonance Logging" by Heaton et al. describe techniques of using diffusion-relaxation time maps derived from NMR data in analyzing formation fluid properties.

Several U.S. patents and Patent Publication disclose methods and apparatus for making NMR measurements in a borehole on fluid samples withdrawn from earth formations. For example, U.S. Pat. No. 6,346,813 B1 issued to Kleinberg discloses an NMR module on the flowline of the wireline formation testers (WFT) (e.g., MDT™ by Schlumberger Technology Corp. (Houston, Tex.)) for determining different fluid properties from magnetic resonance signals; U.S. Pat. No. 6,107,796 issued to M. Prammer discloses apparatus and methods for determining the level of contamination in a formation crude oil sample that may be contaminated by oil-based mud (OBM) filtrate; U.S. Pat. No. 6,111,408 issued to Blades et al. discloses methods and apparatus for measuring the relaxation times (T1 and T2) and the diffusion coefficients (D) of fluids in an NMR module of a fluid sampling tool; U.S. Pat. No. 6,346,813 B1 issued to Kleinberg discloses an NMR module for characterizing fluids in a fluid sampling and testing tool, such as the MDT™ tool; and U.S. Patent Publication No. 2004/0169511A1 by Cao Minh et al. describes a method for interpreting multi-dimensional NMR data.

Despite the development and advancement of various NMR apparatus and methods for determining formation fluid properties based on acquiring formation fluid samples from inside the wellbore, GOR correlation between calculation and measurement has been poor and there remains a need to provide techniques capable of providing a continuous log of formation fluid types and properties in a non-invasive manner without resulting in unnecessary or insufficient sampling.

SUMMARY

The present invention relates to a method for determining oil viscosity and continuous gas oil ration (GOR) from nuclear magnetic resonance logs (NMR). The method includes obtaining a set of NMR data of a portion of the subterranean formation from inside the wellbore without acquiring formation fluid sample; isolating a quantitative reservoir fluid information associated with oil from oil based mud (OBM) using radial profiling of the set of NMR data, wherein the OBM is used for extracting fluid from the underground reservoir; determining gas-oil-ratio (GOR) related information associated with the portion of the subterranean formation from the quantitative reservoir fluid information associated with oil, wherein the GOR related information is determined based on a predetermined model; and performing operations for the oilfield based on the GOR related information.

BRIEF DESCRIPTION OF THE DRAWINGS

So that the above recited features and advantages of the invention can be understood in detail, a more particular description of the invention, briefly summarized above, may be understood by reference to the embodiments thereof that are illustrated in the appended drawings. It is to be noted, however, that the appended drawings illustrate only typical embodiments of this invention and are therefore not to be considered limiting of its scope, for the invention may admit to other equally effective embodiments.

FIGS. 1A-1D depict a simplified schematic view of an oilfield having subterranean formations containing reservoirs therein, the various oilfield operations being performed on the oilfield. FIG. 1A depicts a survey operation being performed by a seismic truck. FIG. 1B depicts a drilling operation being performed by a drilling tool suspended by a rig and advanced into the subterranean formations. FIG. 1C depicts a wireline operation being performed by a wireline tool suspended by the rig and into the wellbore of FIG. 1B. FIG. 1D depicts a production operation being performed by a production tool being deployed from a production unit and into the completed wellbore of FIG. 1C for drawing fluid from the reservoirs into surface facilities.

FIGS. 2A-2D are graphical depictions of data collected by the tools of FIGS. 1A-1D, respectively. FIG. 2A depicts a seismic trace of the subterranean formation of FIG. 1A. FIG. 2B depicts a core test result of the core sample of FIG. 1B. FIG. 2C depicts a well log of the subterranean formation of FIG. 1C. FIG. 2D depicts a production decline curve of fluid flowing through the subterranean formation of FIG. 1D.

FIGS. 9A-9C depict exemplary NMR data graphs with radial profiling technique to distinguish oil from OBM quantitatively in accordance with one or more embodiments of the invention.

DETAILED DESCRIPTION

Figure 3:
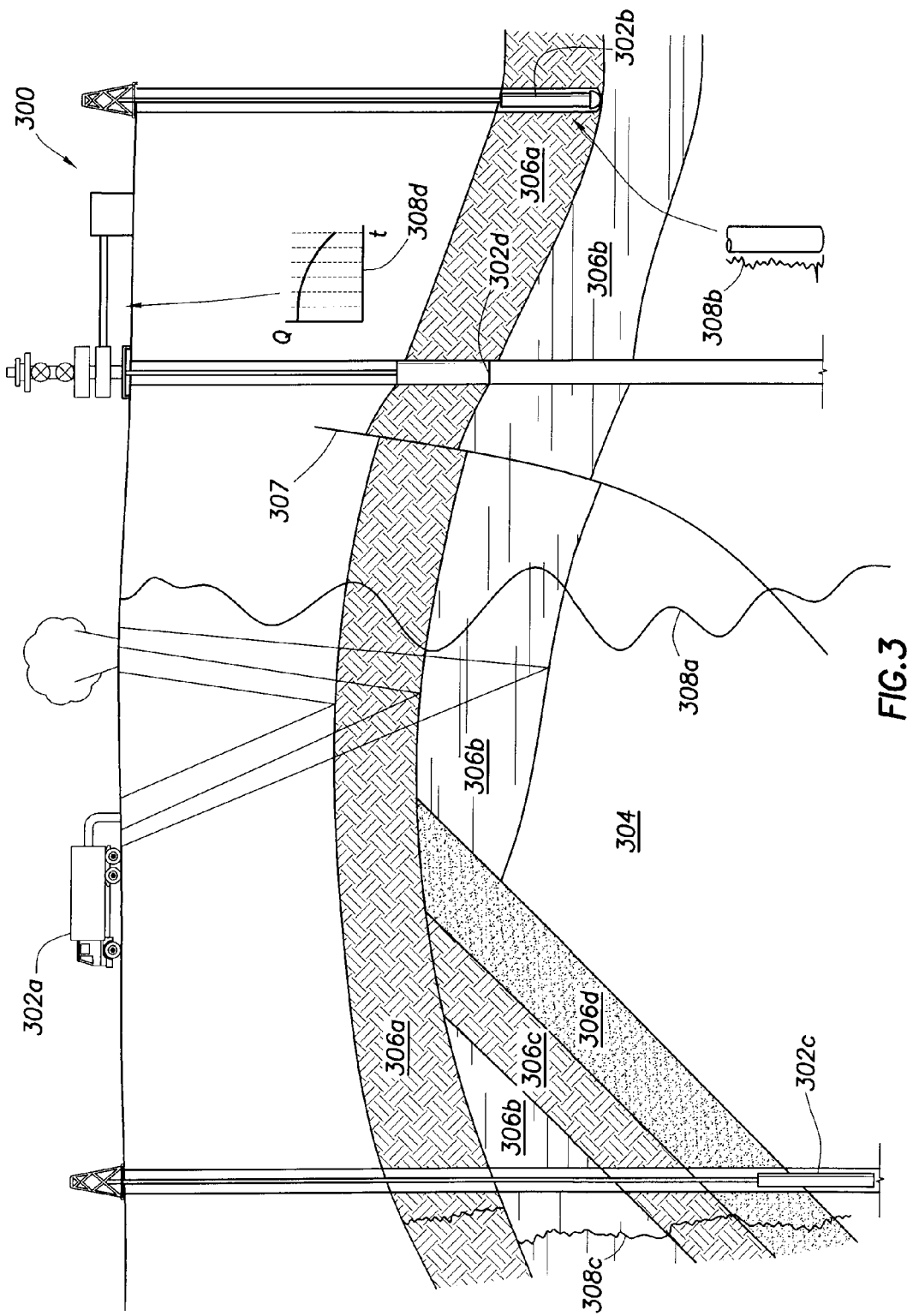
FIG. 3 depicts a schematic view, partially in cross section, of an oilfield having a plurality of data acquisition tools positioned at various locations along the oilfield for collecting data from the subterranean formations in accordance with one or more embodiments of the invention.

Embodiments of the invention are shown in the above-identified figures and described in detail below. In describing the embodiments, like or identical reference numerals are used to identify common or similar elements. The figures are not necessarily to scale and certain features and certain views of the figures may be shown exaggerated in scale or in schematic in the interest of clarity and conciseness.

FIGS. 1A-1D depict simplified, representative, schematic views of an oilfield (100) having subterranean formation (102) containing reservoir (104) therein and depicting various oilfield operations being performed on the oilfield (100). FIG. 1A depicts a survey operation being performed by a survey tool, such as seismic truck (106a) to measure properties of the subterranean formation. The survey operation is a seismic survey operation for producing sound vibrations (112). In FIG. 1A, one such sound vibration (112) generated by a source (110) and reflects off a plurality of horizons (114) in an earth formation (116). The sound vibration(s) (112) is (are) received in by sensors (S), such as geophone-receivers (118), situated on the earth's surface, and the geophone-receivers (118) produce electrical output signals, referred to as data received (120) in FIG. 1.

In response to the received sound vibration(s) (112) representative of different parameters (such as amplitude and/or frequency) of the sound vibration(s) (112), the geophones (118) produce electrical output signals containing data concerning the subterranean formation (102). The data received (120) is provided as input data to a computer (122a) of the seismic truck (106a), and responsive to the input data, the computer (122a) generates a seismic data output record (124). The seismic data may be stored, transmitted or further processed as desired, for example by data reduction.

FIG. 1B depicts a drilling operation being performed by a drilling tools (106b) suspended by a rig (128) and advanced into the subterranean formations (102) to form a wellbore (136). A mud pit (130) is used to draw drilling mud into the drilling tools (106b) via flow line (132) for circulating drilling mud through the drilling tools (106b), up the wellbore and back to the surface. The drilling tools (106b) are advanced into the subterranean formations (102) to reach reservoir (104). Each well may target one or more reservoirs. The drilling tools (106b) are preferably adapted for measuring downhole properties using logging while drilling tools (106b). The logging while drilling tool (106b) may also be adapted for taking a core sample (133) as shown, or removed so that a core sample (133) may be taken using another tool.

A surface unit (134) is used to communicate with the drilling tools (106b) and/or offsite operations. The surface unit (134) is capable of communicating with the drilling tools (106b) to send commands to the drilling tools (106b), and to receive data therefrom. The surface unit (134) is preferably provided with computer facilities for receiving, storing, processing, and/or analyzing data from the oilfield (100). The surface unit (134) collects data generated during the drilling operation and produces data output (135) which may be stored or transmitted. Computer facilities, such as those of the surface unit (134), may be positioned at various locations about the oilfield (100) and/or at remote locations.

Sensors (S), such as gauges, may be positioned about the oilfield to collect data relating to various oilfields operations as described previously As shown, the sensor (S) is positioned in one or more locations in the drilling tools and/or at the rig to measure drilling parameters, such as weight on bit, torque on bit, pressures, temperatures, flow rates, compositions, rotary speed and/or other parameters of the oilfield operation. Sensor (S) may also be positioned in one or more locations in the circulating system.

The data gathered by the sensors (S) may be collected by the surface unit (134) and/or other data collection sources for analysis or other processing. The data collected by the sensors (S) may be used alone or in combination with other data. The data may be collected in one or more databases and/or all or transmitted onsite or offsite. All or select portions of the data may be selectively used for analyzing and/or predicting oilfield operations of the current and/or other wellbores. The data may be may be historical data, real time data, or combinations thereof. The real time data may be used in real time, or stored for later use. The data may also be combined with historical data or other inputs for further analysis. The data may be stored in separate databases or combined into a single database.

Data outputs from the various sensors (S) positioned about the oilfield may be processed for use. The data may be historical data, real time data, or combinations thereof. The real time data may be used in real time, or stored for later use. The data may also be combined with historical data or other inputs for further analysis. The data may be housed in separate databases, or combined into a single database.

The collected data may be used to perform analysis, such as modeling operations. For example, the seismic data output may be used to perform geological, geophysical, and/or reservoir engineering. The reservoir, wellbore, surface and/or process data may be used to perform reservoir, wellbore, geological, geophysical or other simulations. The data outputs from the oilfield operation may be generated directly from the sensors (S), or after some preprocessing or modeling. These data outputs may act as inputs for further analysis.

The data is collected and stored at the surface unit (134). One or more surface units (134) may be located at the oilfield (100), or connected remotely thereto. The surface unit (134) may be a single unit, or a complex network of units used to perform the necessary data management functions throughout the oilfield (100). The surface unit (134) may be a manual or automatic system. The surface unit (134) may be operated and/or adjusted by a user.

The surface unit (134) may be provided with a transceiver (137) to allow communications between the surface unit (134) and various portions of the oilfield (100) or other locations. The surface unit (134) may also be provided with or functionally connected to one or more controllers for actuating mechanisms at the oilfield (100). The surface unit (134) may then send command signals to the oilfield (100) in response to data received. The surface unit (134) may receive commands via the transceiver or may itself execute commands to the controller. A processor (not shown) may be provided to analyze the data (locally or remotely) and make the decisions and/or actuate the controller. In this manner, the oilfield (100) may be selectively adjusted based on the data collected. This technique may be used to optimize portions of the oilfield operation, such as controlling drilling, weight on bit, pump rates or other parameters. These adjustments may be made automatically based on computer protocol, and/or manually by an operator. In some cases, well plans may be adjusted to select optimum operating conditions, or to avoid problems.

FIG. 1C depicts a wireline operation being performed by a wireline tool (106c) suspended by the rig (128) and into the wellbore (136) of FIG. 1B. The wireline tool (106c) is preferably adapted for deployment into a wellbore (136) for generating well logs, performing downhole tests and/or collecting samples. The wireline tool (106c) may be used to provide another method and apparatus for performing a seismic survey operation. The wireline tool (106c) of FIG. 1C may, for example, have an explosive, radioactive, electrical, or acoustic energy source (144) that sends and/or receives electrical signals to the surrounding subterranean formations (102) and fluids therein.

The wireline tool (106c) may be operatively connected to, for example, the geophones (118) stored in the computer (122a) of the seismic truck (106a) of FIG. 1A. The wireline tool (106c) may also provide data to the surface unit (134). The surface unit (134) collects data generated during the wireline operation and produces data output (135) that may be stored or transmitted. The wireline tool (106c) may be positioned at various depths in the wellbore (136) to provide a survey or other information relating to the subterranean formation (102).

Sensors (S), such as gauges, may be positioned about the oilfield to collect data relating to various oilfield operations as described previously. As shown, the sensor (S) is positioned in the wireline tool (106c) to measure downhole parameters, which relate to, for example porosity, permeability, fluid composition, and/or other parameters of the oilfield operation.

FIG. 1D depicts a production operation being performed by a production tool (106d) deployed from a production unit or christmas tree (129) and into the completed wellbore (136) of FIG. 1C for drawing fluid from the downhole reservoirs into the surface facilities (142). Fluid flows from reservoir (104) through perforations in the casing (not shown) and into the production tool (106d) in the wellbore (136) and to the surface facilities (142) via a gathering network (146).

Sensors (S), such as gauges, may be positioned about the oilfield to collect data relating to various oilfield operations as described previously. As shown, the sensor (S) may be positioned in the production tool (106d) or associated equipment, such as the christmas tree (129), gathering network (146), surface facilities (142) and/or the production facility, to measure fluid parameters, such as fluid composition, flow rates, pressures, temperatures, and/or other parameters of the production operation.

While only simplified wellsite configurations are shown, it will be appreciated that the oilfield may cover a portion of land, sea and/or water locations that hosts one or more wellsites. Production may also include injection wells (not shown) for added recovery. One or more gathering facilities may be operatively connected to one or more of the wellsites for selectively collecting downhole fluids from the wellsite(s).

While FIGS. 1B-1D depict tools used to measure properties of an oilfield (100), it will be appreciated that the tools may be used in connection with non-oilfield operations, such as mines, aquifers, storage or other subterranean facilities. Also, while certain data acquisition tools are depicted, it will be appreciated that various measurement tools capable of sensing parameters, such as seismic two-way travel time, density, resistivity, production rate, etc., of the subterranean formation (102) and/or its geological formations may be used. Various sensors (S) may be located at various positions along the wellbore and/or the monitoring tools to collect and/or monitor the desired data. Other sources of data may also be provided from offsite locations.

The oilfield configuration in FIGS. 1A-1D are intended to provide a brief description of an example of an oilfield usable with the present invention. Part, or all, of the oilfield (100) may be on land and/or sea. Also, while a single oilfield measured at a single location is depicted, the present invention may be used with any combination of one or more oilfields (100), one or more processing facilities, and one or more wellsites.

FIGS. 2A-2D are graphical depictions of examples of data collected by the tools of FIGS. 1A-D, respectively. FIG. 2A depicts a seismic trace (202) of the subterranean formation of FIG. 1A taken by seismic truck (106a). The seismic trace may be used to provide data, such as a two-way response over a period of time. FIG. 2B depicts a core sample (133) taken by the drilling tools (106b). The core sample (133) may be used to provide data, such as a graph of the density, porosity, permeability or other physical property of the core sample (133) over the length of the core. Tests for density and viscosity may be performed on the fluids in the core at varying pressures and temperatures. FIG. 2C depicts a well log (204) of the subterranean formation (102) of FIG. 1C taken by the wireline tool (106c). The wireline log typically provides a resistivity or other measurement of the formations at various depts. FIG. 2D depicts a production decline curve or graph (206) of fluid flowing through the subterranean formation (102) of FIG. 1D measured at the surface facilities (142). The production decline curve (206) typically provides the production rate (Q) as a function of time (t).

The respective graphs of FIGS. 2A-2C depict examples of static measurements that may describe information about the physical characteristics of the formation and reservoirs contained therein. These measurements may be analyzed to better define the properties of the formation(s) and/or determine the accuracy of the measurements and/or for checking for errors. The plots of each of the respective measurements may be aligned and scaled for comparison and verification of the properties.

FIG. 2D depicts an example of a dynamic measurement of the fluid properties through the wellbore. As the fluid flows through the wellbore, measurements are taken of fluid properties, such as flow rates, pressures, composition, etc. As described below, the static and dynamic measurements may be analyzed and used to generate models of the subterranean formation to determine characteristics thereof. Similar measurements may also be used to measure changes in formation aspects over time.

FIG. 3 is a schematic view, partially in cross section of an oilfield (300) having data acquisition tools (302a), (302b), (302c), and (302d) positioned at various locations along the oilfield for collecting data of a subterranean formation (304). The data acquisition tools (302a-302d) may be the same as data acquisition tools (106a-106d) of FIGS. 1A-1D, respectively, or others not depicted. As shown, the data acquisition tools (302a-302d) generate data plots or measurements (308a-308d), respectively. These data plots are depicted along the oilfield to demonstrate the data generated by various operations.

Data plots (308a-308c) are examples of static data plots that may be generated by the data acquisition tools (302a-302d), respectively. Static data plot (308a) is a seismic two-way response time and may be the same as the seismic trace (202) of FIG. 2A. Static plot (308b) is core sample data measured from a core sample of the formation (304), similar to the core sample (133) of FIG. 2B. Static data plot (308c) is a logging trace, similar to the well log (204) of FIG. 2C. Production decline curve or graph (308d) is a dynamic data plot of the fluid flow rate over time, similar to the graph (206) of FIG. 2D. Other data may also be collected, such as historical data, user inputs, economic information, and/or other measurement data and other parameters of interest.

The subterranean formation (304) has a plurality of geological formations (306a-306d). As shown, the structure has several formations or layers, including a shale layer (306a), a carbonate layer (306b), a shale layer (306c) and a sand layer (306d). A fault line (307) extends through the layers (306a, 306b). The static data acquisition tools are preferably adapted to take measurements and detect the characteristics of the formations.

While a specific subterranean formation (304) with specific geological structures are depicted, it will be appreciated that the oilfield may contain a variety of geological structures and/or formations, sometimes having extreme complexity. In some locations, typically below the water line, fluid may occupy pore spaces of the formations. Each of the measurement devices may be used to measure properties of the formations and/or its geological features. While each acquisition tool is shown as being in specific locations in the oilfield, it will be appreciated that one or more types of measurement may be taken at one or more location across one or more oilfields or other locations for comparison and/or analysis.

The data collected from various sources, such as the data acquisition tools of FIG. 3, may then be processed and/or evaluated. Typically, seismic data displayed in the static data plot (308a) from the data acquisition tool (302a) is used by a geophysicist to determine characteristics of the subterranean formations (304) and features. Core data shown in static plot (308b) and/or log data from the well log (308c) is typically used by a geologist to determine various characteristics of the subterranean formation (304). Production data from the graph (308d) is typically used by the reservoir engineer to determine fluid flow reservoir characteristics. The data analyzed by the geologist, geophysicist and the reservoir engineer may be analyzed using modeling techniques. Examples of modeling techniques are described in U.S. Pat. No. 5,992,519, WO2004/049216, WO1999/064896, U.S. Pat. No. 6,313,837, US2003/0216897, U.S. Pat. No. 7,248,259, US2005/0149307 and US2006/0197759. Systems for performing such modeling techniques are described, for example, in issued U.S. Pat. No. 7,248,259, the entire contents of which are hereby incorporated by reference.

Figure 4:
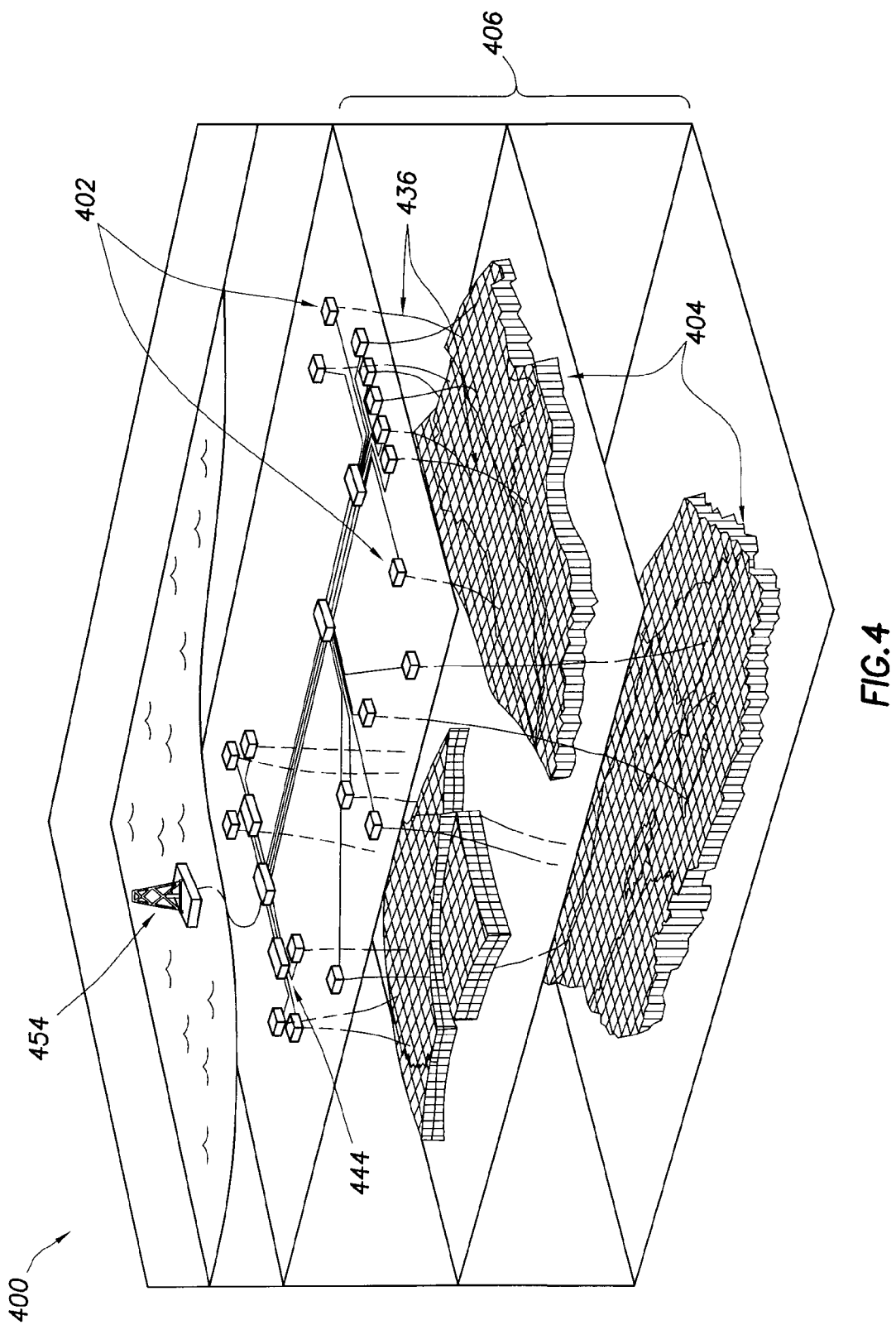
FIG. 4 depicts an exemplary schematic view of an oilfield having a plurality of wellsites for producing hydrocarbons from the subterranean formation in accordance with one or more embodiments of the invention.

FIG. 4 shows an oilfield (400) for performing production operations. As shown, the oilfield has a plurality of wellsites (402) operatively connected to a central processing facility (454). The oilfield configuration of FIG. 4 is not intended to limit the scope of the invention. Part or all of the oilfield may be on land and/or sea. Also, while a single oilfield with a single processing facility and a plurality of wellsites is depicted, any combination of one or more oilfields, one or more processing facilities and one or more wellsites may be present.

Each wellsite (402) has equipment that forms a wellbore (436) into the earth. The wellbores extend through subterranean formations (406) including reservoirs (404). These reservoirs (404) contain fluids, such as hydrocarbons. The wellsites draw fluid from the reservoirs and pass them to the processing facilities via surface networks (444). The surface networks (444) have tubing and control mechanisms for controlling the flow of fluids from the wellsite to the processing facility (454).

Acquisition of NMR measurements according to embodiments of the invention may be accomplished with various methods of NMR measurements known in the art. For example, the measurements may be performed in a laboratory using a sample (e.g., as shown in FIG. 2B) removed from an earth formation. Alternatively, the NMR measurements may be performed in a logging operation using a wireline tool, a logging-while-drilling or measurement-while-drilling tool, or a formation tester.

Figures 5, 6:
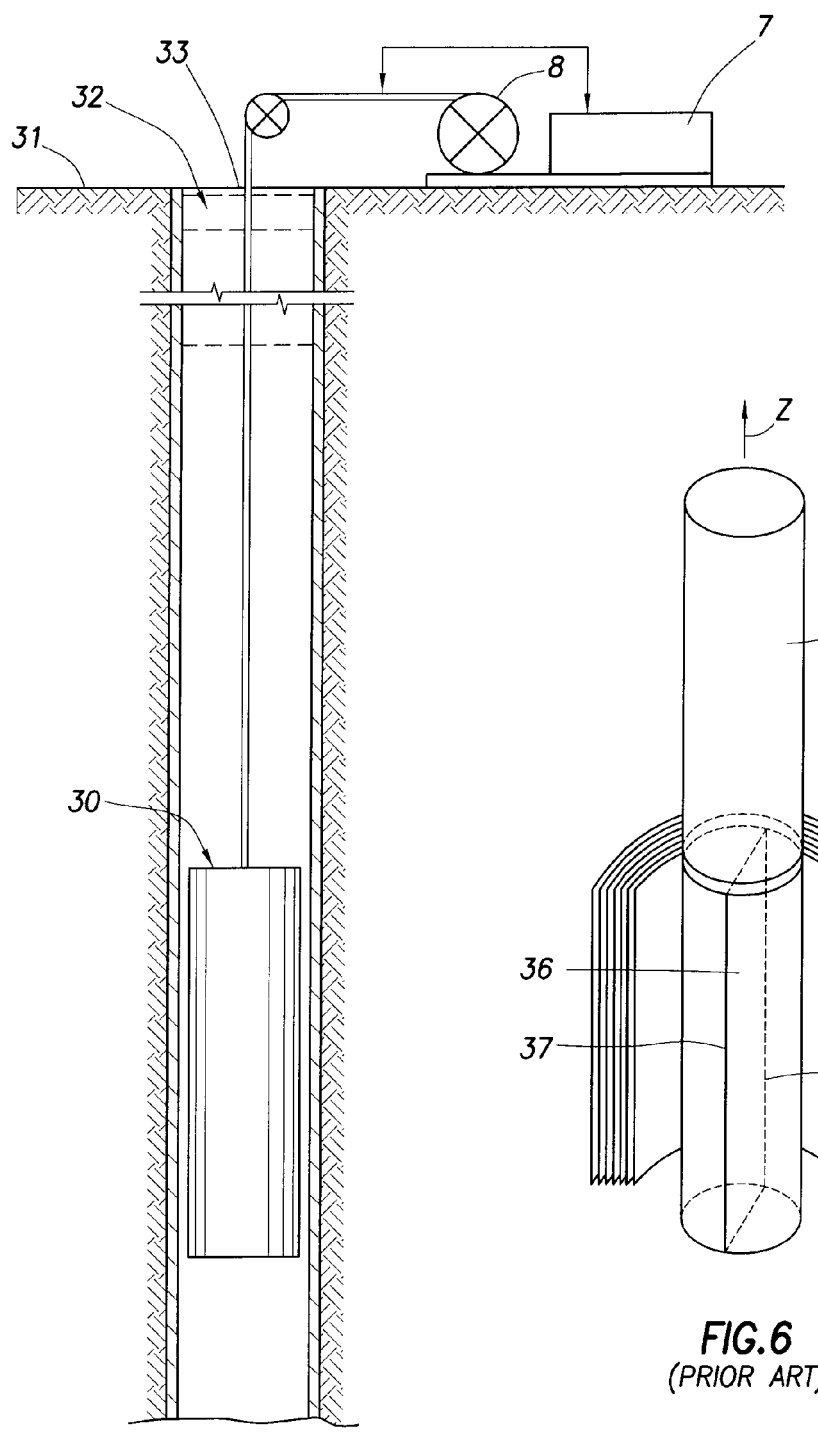
FIG. 5 depicts an exemplary downhole NMR data acquisition system.
FIG. 6 depicts a more detailed diagram an exemplary downhole NMR data acquisition system shown in FIG. 5 in accordance with one or more embodiments of the invention.

FIG. 5 depicts a schematic of an NMR logging system. In FIG. 5, a NMR logging tool (30) for investigating subterranean formations (31) traversed by a borehole (32) is shown. The NMR logging device (30) is suspended in the borehole (32) on an armored cable (33), the length of which substantially determines the relative axial depth of the device (30). The cable length is controlled by suitable means at the surface such as a drum and winch mechanism (8). Surface equipment (7) can be of conventional type and can include a processor subsystem which communicates with downhole equipment including NMR logging device (30).

The NMR logging device (30) can be any suitable nuclear magnetic resonance logging device; it may be one for use in wireline logging applications as shown in FIG. 1C, or one that can be used in logging-while-drilling (LWD) or measurement-while-drilling (MWD) applications as shown in FIG. 1B. In addition, the NMR logging device (30) may be part of any formation tester known in the art, such as that sold under the trade name of MDT™ by Schlumberger Technology Corporation (Houston, Tex.). The NMR logging device (30) typically includes a means for producing a static magnetic field in the formations, and a radio frequency (RF) antenna means for producing pulses of magnetic field in the formations and for receiving the spin echoes from the formations. The means for producing a static magnetic field may comprise a permanent magnet or magnet array, and the RF antenna means for producing pulses of magnetic field and receiving spin echoes from the formations may comprise one or more RF antennas.

FIG. 6 illustrates a schematic of some of the components of one type of NMR logging device (30). FIG. 6 shows a first centralized magnet or magnet array (36) and an RF antenna (37), which may be a suitably oriented coil or coils. FIG. 6 also illustrates a general representation of closely spaced cylindrical thin shells, (38-1), (38-2) . . . (38-N), that can be frequency selected in a multi-frequency logging operation. One such device is disclosed in U.S. Pat. No. 4,710,713. In FIG. 6, another magnet or magnet array (39) is shown. Magnet array (39) may be used to pre-polarize the earth formation ahead of the investigation region as the logging device (30) is raised in the borehole in the direction of arrow (Z). Examples of such devices are disclosed in U.S. Pat. Nos. 5,055,788 and 3,597,681.

Figure 7:
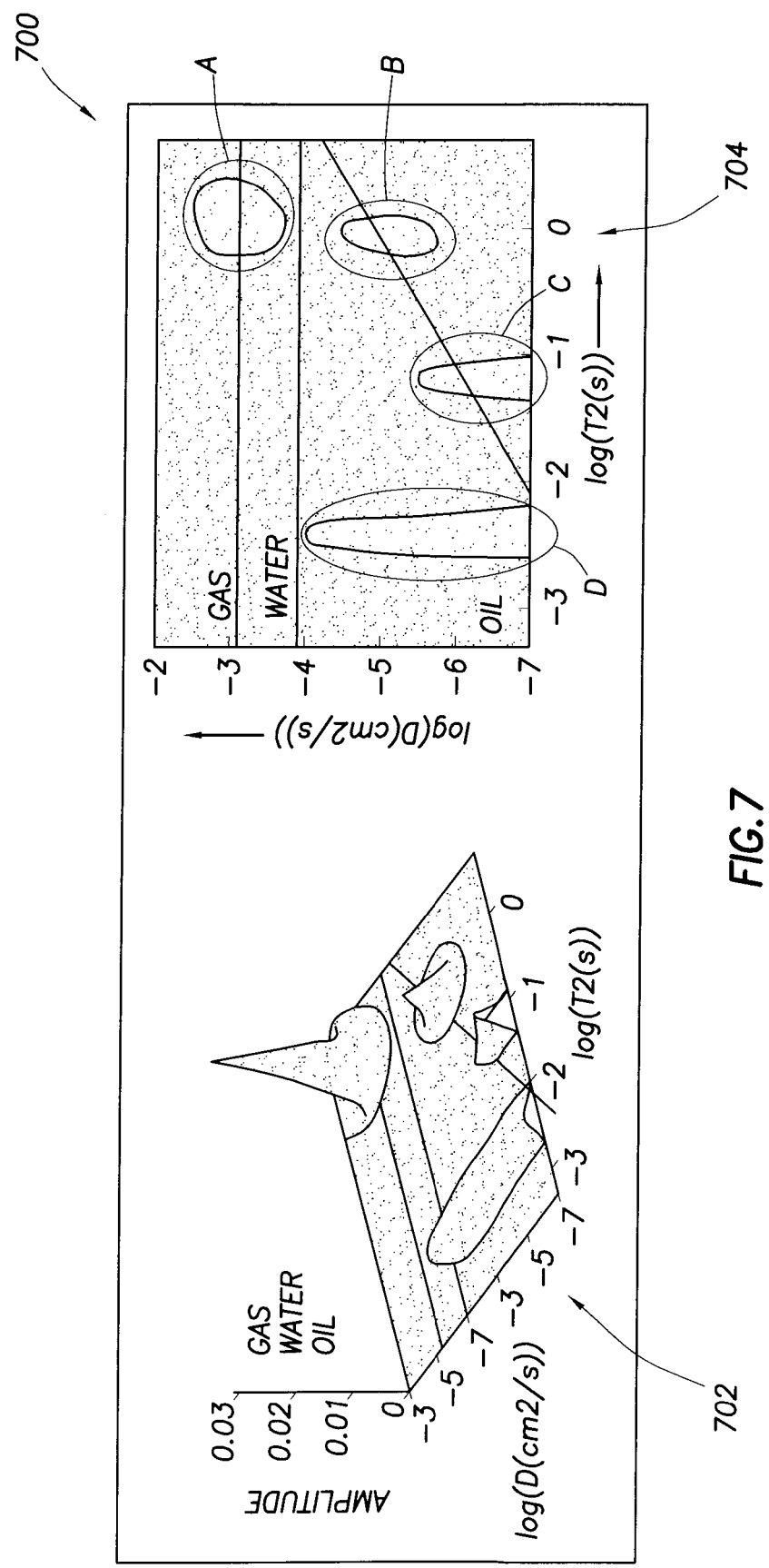
FIG. 7 depicts exemplary multi-dimensional maps or graphs for displaying NMR data in accordance with one or more embodiments of the invention.

Turning now to FIG. 7, shown is an exemplary diffusion-relaxation time T2 (D-T2) map (700) with NMR spin echo data presented as amplitudes versus diffusion (D) map (702) in a left panel and a relaxation time (T2) map (704) in a right panel. The map (702) shown in the left panel is a three-axis perspective view. The map (704) shown in the right panel provides a more practical representation of D-T2 map as a two-axis map. However, it should be noted that the disclosed methods may be applied a dataset having any number of dimensions, 2-D, 3-D, 4-D, etc. Furthermore, it should be noted that although D-T2 maps are discussed herein for exemplary purposes, the disclosed methods can be equally as effective in obtaining quantitative formation evaluation answers based on many other combinations of NMR data properties (D, T1, T2, T1/T2, etc.).

In the context of the two-axis D-T2 map, the diffusion amplitude is represented according to a color-coding scheme (not shown). The differences of diffusion properties among gas, water, and various viscosity oils are captured by the D-T2 map and shown as separate and distinct peaks. Specifically, the color grouping at A, also herein referred to as an artifact or a fluid instance, represents the probable detection of a first fluid. Similarly, the lighter color groupings or fluid instances at B, C, and D also represent the probable detection of three additional fluids. The theoretical responses of water, oil, and gas are overlaid on the maps to help the interpretation. Thus, for grouping or instance A, it is likely that the fluid is gas because its peak lies near the theoretical gas diffusion value. For groupings B and C, it is likely the fluids are varying viscosities or phases of oil, lying along the theoretical oil diffusion line. Finally, it is likely that grouping or instance D is water subject to restricted diffusion.

Figure 8:
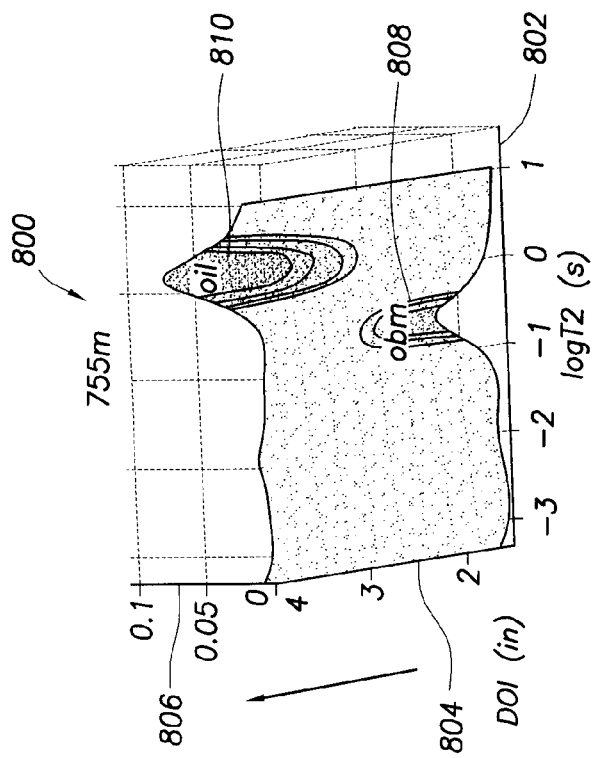
FIG. 8 depicts an exemplary NMR data graphs with radial profiling technique to distinguish oil from oil based mud (OBM) in accordance with one or more embodiments of the invention.

FIG. 8 shows an exemplary NMR data graph (800) with radial profiling technique to distinguish oil from OBM. Here, a first axis (802) labeled "logT2(s)" represents a log scale of relaxation time T2 measured in seconds. A second axis (804) labeled DOT(in) represents the radial profiling depth measured in inches. A third axis (806) with a scale ranging from zero to 0.1 represents NMR amplitude, which is also reflected in the visual enhancement of the data graph using a color-coding scheme (not shown).

Typically, both OBM filtrate and native oil found inside the subterranean formations near the wellbore are stable compounds that are in thermodynamics equilibrium. In general, the slow fluid filtration through a mud cake does not provide enough external energy to mix the OBM and oil. The NMR data graph as shown in FIG. 8 can be used to visually separate OBM from oil around the wellbore. In the case where the viscosities of OBM and oil are distinctly different, the color groupings labeled "obm" (808) and "oil" (810) may be seen as separate instances in the NMR data graph as shown in FIG. 8. In the case where viscosities of OBM and oil are similar, the NMR data graph interpretation needs to rely on the changes along the radial direction away from the wellbore into the formation. Typically, invading OBM decreases with this radial depth while the oil/water volumes increase with the radial depth.

FIGS. 9A-9C show exemplary NMR data graphs (900) with radial profiling technique to distinguish oil from OBM quantitatively. As shown, the leftmost tracks (902) of FIGS. 9A-9C depict vertical depth log of NMR relaxation time data where the portion highlighted within the circle (904) may point to a reservoir sand section imbedded in shale sections penetrated by the wellbore. The center tracks (906) depict vertical depth log of NMR diffusion data. The rightmost tracks (908) depict volumetric breakdown among oil (910) (shown as left slanted cross hatch and may be depicted in green), OBM (912) (shown as right slant cross hatch and may be depicted in brown), and water (914) (which may be depicted in white) where the solid black traces (916) represent the total fluid volume. As shown in FIGS. 9A-9C, the oil (or hydrocarbon) occupies larger portions of the volumetric breakdown as the radial investigation depth increases from 1.5 inch to 4.0 inch into the formation. For example, in FIG. 9A, at 1.5 inch depth of the radial investigation, the hydrocarbon is 80% OBM and 20% oil. In FIG. 9B, at 2.7 inch depth of the radial investigation, the hydrocarbon is 50% OBM and 50% oil, and in FIG. 9C, at 4.0 inch depth of the radial investigation, the hydrocarbon is 5% OBM and 95% oil. The volumetric breakdown among oil, OBM, and water can be derived quantitatively from the NMR data, for example the diffusion and relaxation time depicted in the leftmost and center tracks (902) and (906), respectively.

Figure 10:
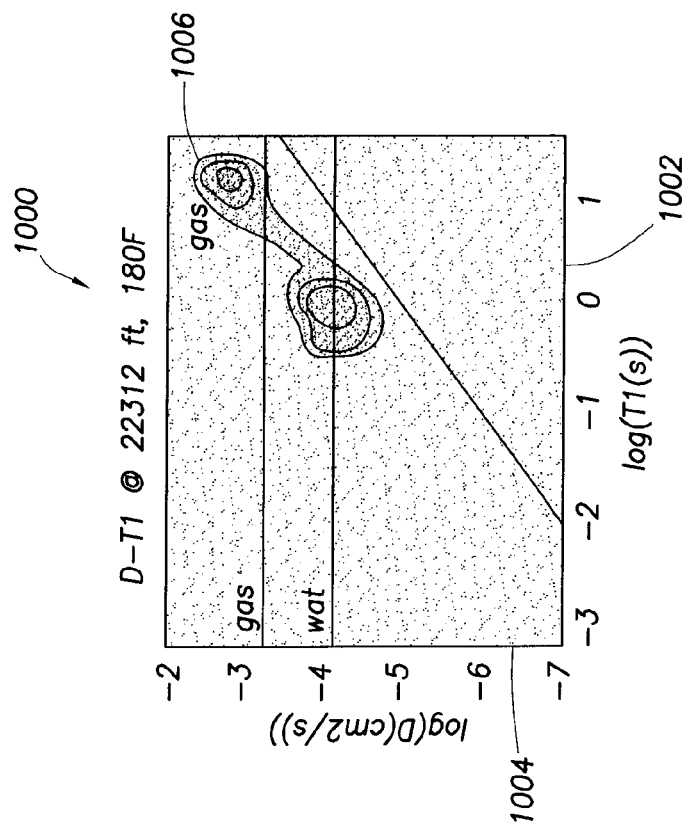
FIG. 10 depicts an exemplary diffusion-relaxation map for displaying NMR data in accordance with one or more embodiments of the invention.

FIG. 10 shows an exemplary diffusion-relaxation T1 (D-T1) map (1000) for displaying NMR data. Gas has relatively longer NMR relaxation time T1 (1002) and higher diffusion D (1004), hence its presence typically shows toward the top right hand corner of the D-T1 map, such as the color grouping labeled as "gas" (1006) shown in FIG. 10. Typically, gas volume may be interactively estimated by manipulating the D-T1 map, for example using an input device, such as a computer mouse.

Figure 11:
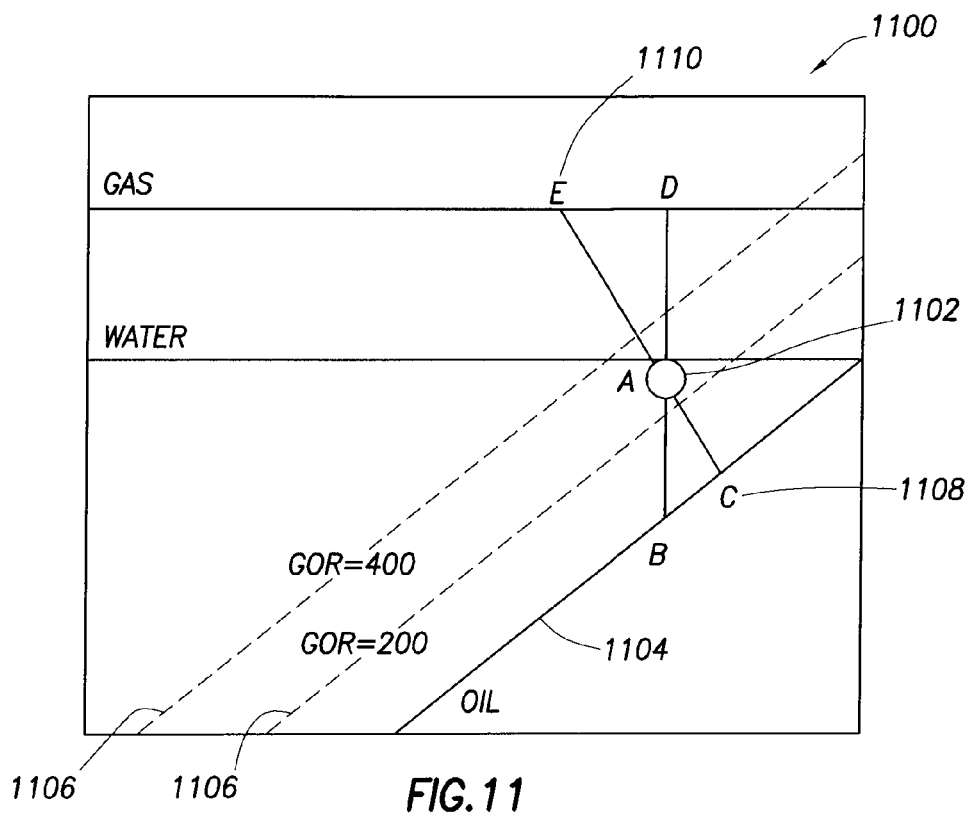
FIG. 11 depicts a schematic diagram of the diffusion-relaxation map in accordance with one or more embodiments of the invention.

Alternatively, gas volume can also be estimated as depicted in a schematic representation of diffusion-relaxation time map (1100) depicted in FIG. 11. As shown in FIG. 11, point (A) (1102) represents NMR data color grouping for a fluid under study. The solid line (1104) (which may be depicted in green) represents NMR data from dead oil (i.e., oil containing negligible amount of dissolved gas) and is termed "dead oil line". The dashed lines (1106) (which may be depicted in green) to the left and upper sides of the dead oil line represent oil with increasing amount of dissolved gas (i.e., live oil), for example with GORs of 200 and 400, respectively. In one theory, a dead oil point (C) (1108) marches through point (A)(1102) with increasing GOR towards gas point (E) (1110) where the fluid becomes 100% gas with decreasing relaxation time. In a second theory, the dead oil point (C) marches towards the gas line with increasing relaxation time.

Secondary effects can cause the marching path to curve in an S-shape from dead oil point (C) (1108) to gas point (E) (1110). However, in the case where the fluid under study exhibits relatively long NMR relaxation time T1 making the straight line distance between (C) and (E) correspondingly small, the gas saturation ($S_g$) at data point (A) (1102) may be estimated using a straight line approximation, yielding $S_g$=AC/CE. Furthermore, AC/CE=AB/DB based on the similar triangles ABC and ADE, therefore $S_g$=AB/DB (where B and D are constant relaxation time in the evolution from dead oil to free gas). Note that the schematic diagram of FIG. 11 is in logarithmic scale for both diffusion and relaxation time. Analytically, AB/DB is the graphical solution of the gas saturation as computed by the diffusion log mean (DCLM) equations for an oil-gas model known by one skilled in the art. Accordingly, the gas saturation of a fluid understudy can be estimated based on the DCLM approach as applied to the diffusion-relaxation time map.

Figure 12:
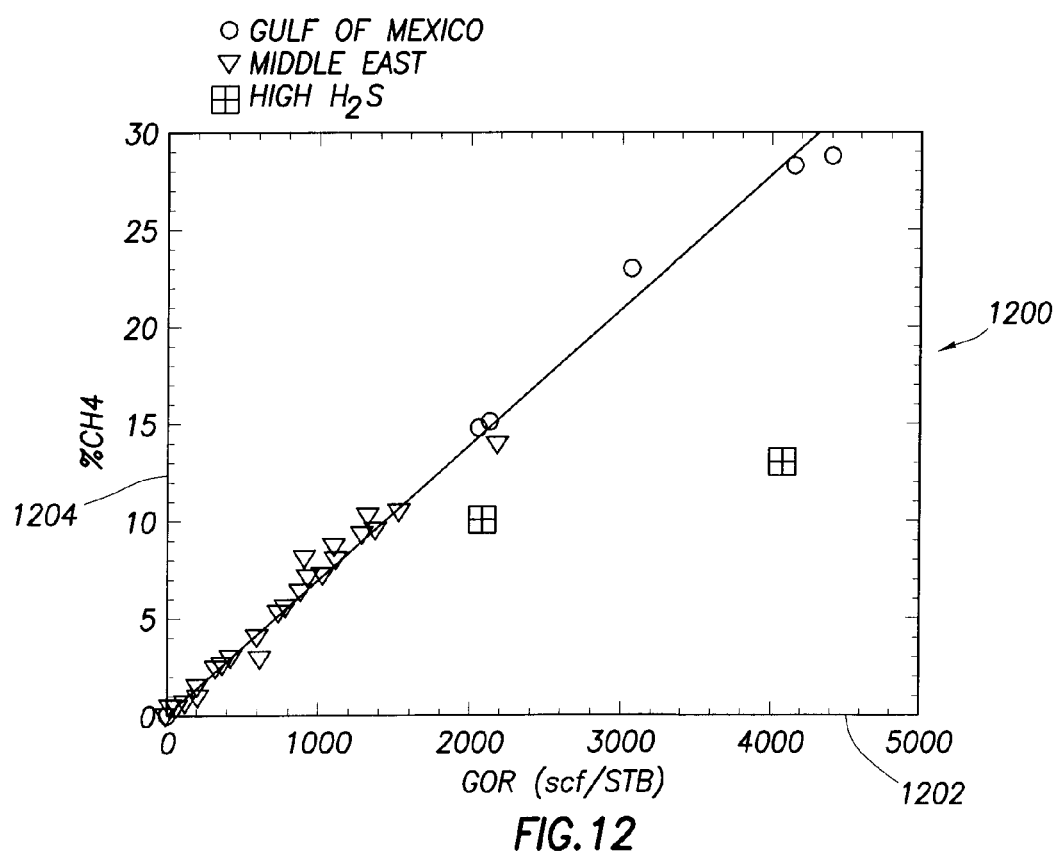
FIG. 12 depicts an exemplary graph depicting fluid properties obtained from non-NMR measurements in accordance with one or more embodiments of the invention.

FIG. 12 depicts an exemplary graph (1200) depicting fluid properties obtained from non-NMR measurements, performed for example, by wireline formation tester (WFT) equipments (such as MDT™) on physical formation fluid samples. As shown, the x-axis (1202) represents GOR while the y-axis (1204) represents mass percentage (or gas saturation $S_g$) of methane ($CH_4$) in the formation fluid samples under study. On the graph, 12, the gas percentage in oil is proportional to the GOR as observed by the MDT measurements. This observation leads to an empirical equation $GOR=a*(V_{gas}/V_{oil})/(oil\ viscosity)^b$ where "a" and "b" are constants and $V_{gas}/V_{oil}$ is the gas saturation $S_g$. The constant "a" represents the conversion from volume to mass and surface to downhole expansion. The constant "b" controls the inverse dependency of the computed GOR on oil viscosity. It is equivalent to the dependency on relaxation time T1 or T2 as viscosity is inversely proportional to the relaxation time. For a given gas saturation, the viscosity in the empirical equation takes into account the temperature effect (i.e., higher temperature lowers viscosity, hence increases GOR estimation) and heavy oil effect (i.e., increasing viscosity lowers GOR estimation).

Figure 13:
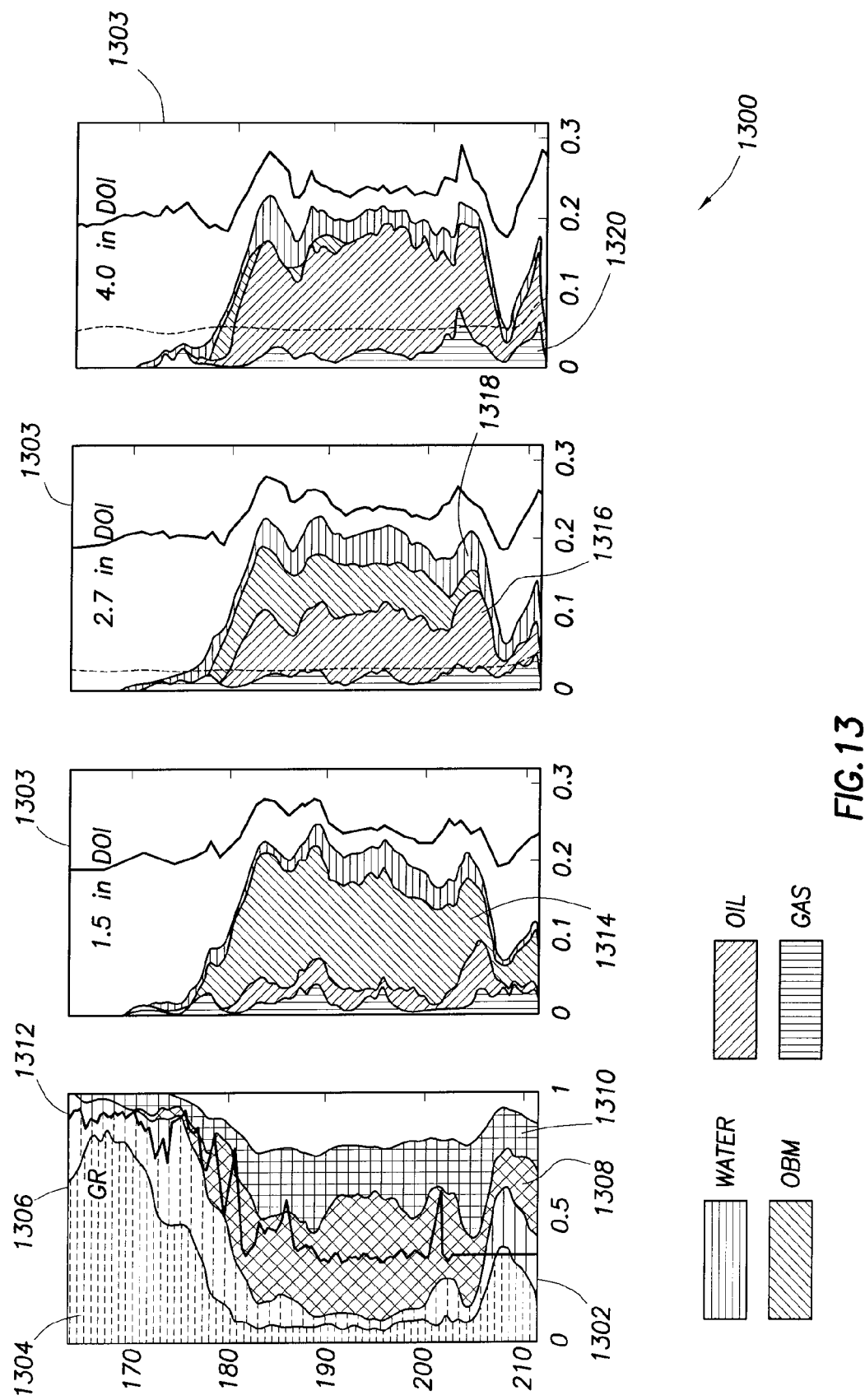
FIGS. 13 and 14 depict exemplary wellbore logging data and analysis for determining continuous GOR in accordance with one or more embodiments of the invention.
Figure 14:
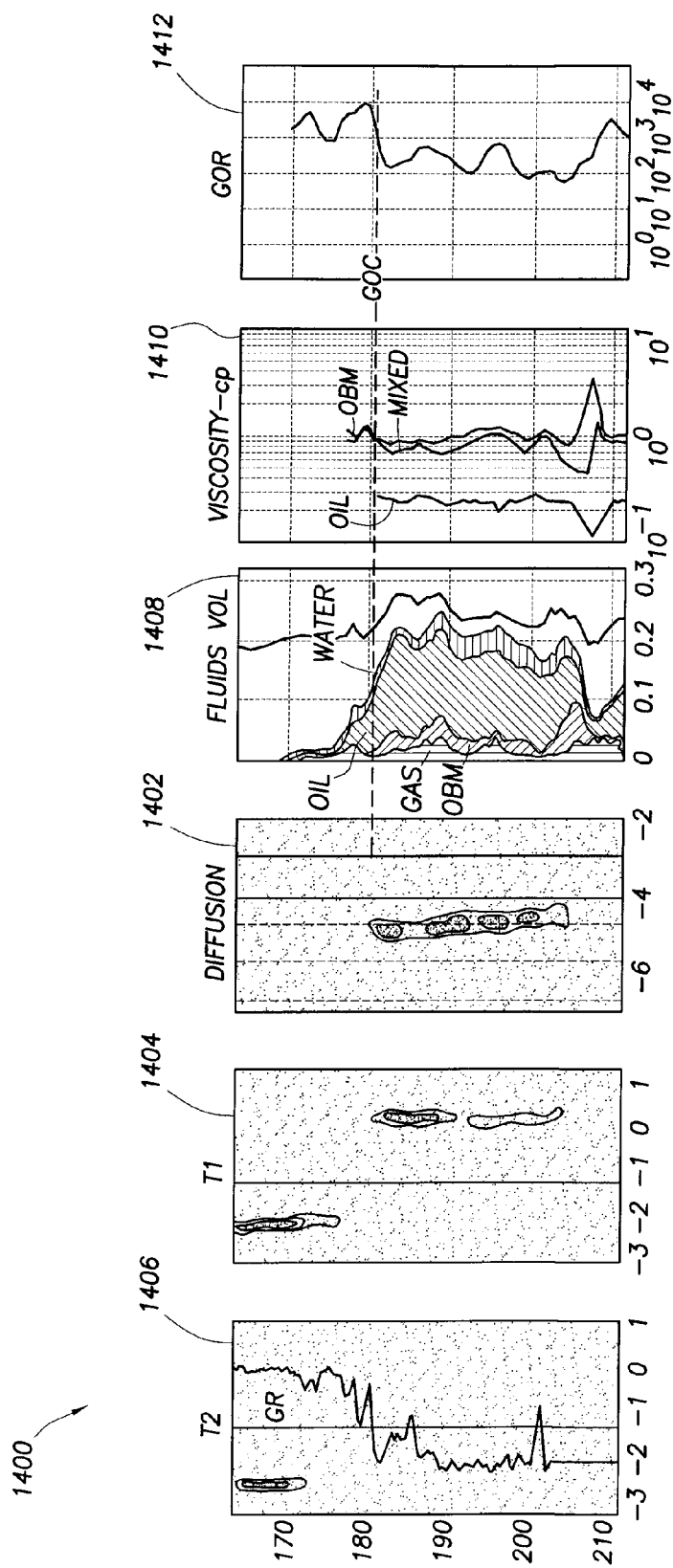

FIGS. 13 and 14 depict exemplary wellbore logging data and analysis for determining continuous GOR. FIG. 13 depicts logging data and analysis (1300) which includes a gamma-ray log (1302) labeled "GR" over the depth range from less than 170 m to 210 m, which likely indicates a shale section above 170 m transitioning into a reservoir sand section below 185 m with a thin-bedded zone in between. As shown, area (1304) (which may be depicted in dark gray) represents the clay volume associated with T2<3 ms. Area (1306) (which may be depicted in light gray) represents the silt volume associated with 3 ms<T2<33 ms such that the total gray area represents the shale volume. Area (1308) (which may be depicted in orange) is the sand/free fluid volume associated with 33 ms<T2<300 ms. Area (1310) (which may be depicted in yellow) is the sand/free fluid associated with T2>300 ms. The solid line (1312) represents the GR log.

FIG. 13 also includes three fluid volumetric breakdown charts (1303) derived from radial profiling of NMR data as illustrated with respect to FIG. 9 above. The three fluid volumetric breakdown charts (1303) are based on radial depth of 1.5 inches, 2.7 inches, and 4.0 inches, respectively. As shown in FIG. 13, volumes of OBM (1314) (which may be depicted in brown) and oil (1316) (which may be depicted in green) are separately identified with increasing depth of investigation. Water (1318) (which may be depicted in blue) and gas (1320) (which may be depicted in red) are also depicted in the charts. However, there is no clear indication from these charts alone as to whether there is a gas cap exhibiting a gas oil contact (GOC) or where the location of the gas cap may be if one does exist.

FIG. 14 includes NMR data logs (1400) of diffusion (1402) and relaxation times T1 (1404) and T2 (1406), as well as data logs depicting fluid volumetric breakdown (1408), viscosity (1410), and GOR (1412) derived from the NMR data. As shown in FIG. 14, the oil viscosity is three times lower than the OBM viscosity and the continuous GOR clearly shows a nearly two orders of magnitude drop from $10^4$ to $10^2$ near depth of 180 m. The significant drop in GOR indicates the GOC, which occurs in the thin-bedded zone identified by the gamma ray log superimposed on the relaxation time T2 log on the leftmost track. The GOC would have been impossible to detect using prior art techniques such as density-neutron or pressure gradient techniques.

Figure 15:
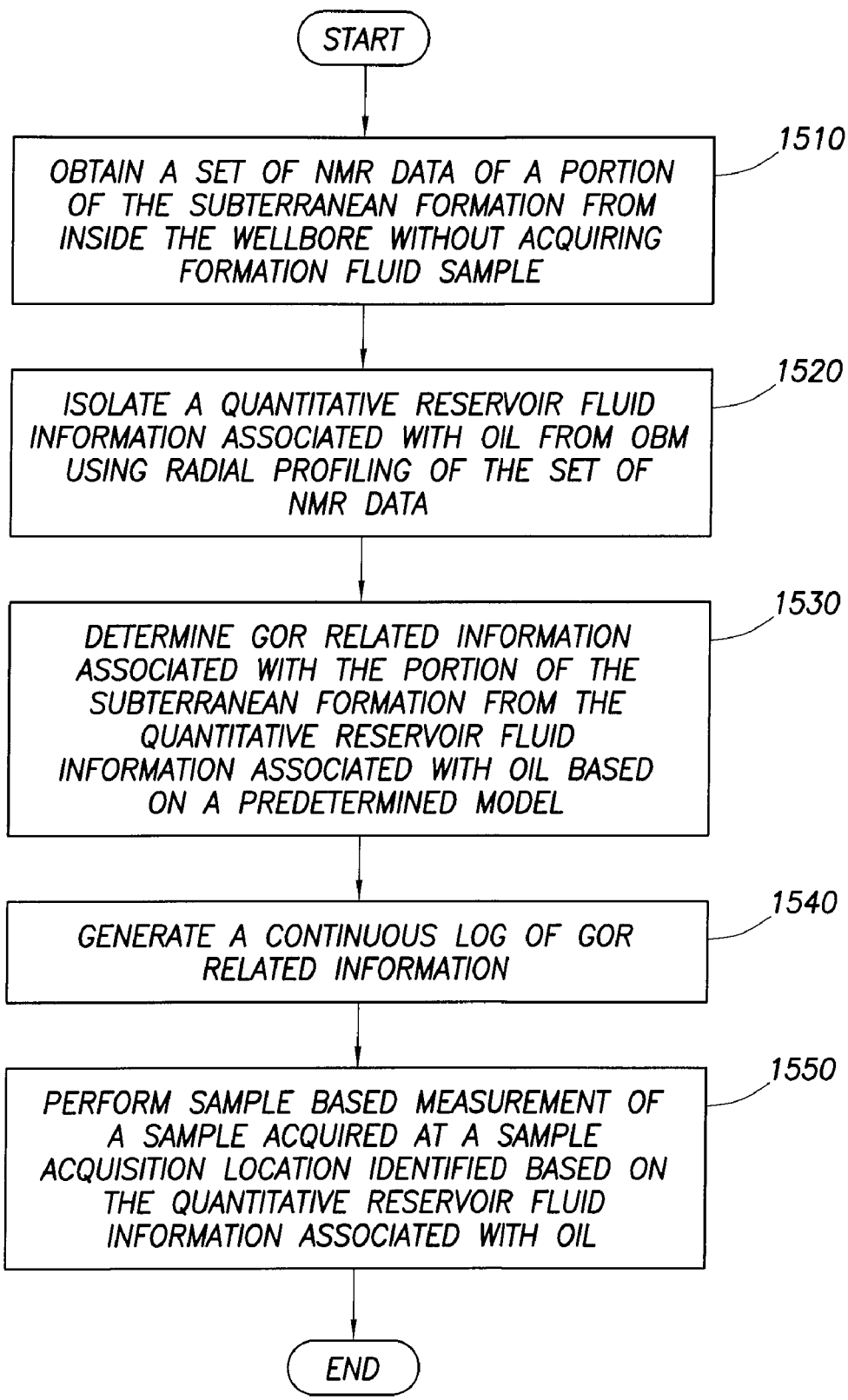
FIG. 15 depicts a flowchart depicting a method of determining continuous GOR in an oil field in accordance with one or more embodiments of the invention.

FIG. 15 shows a flowchart depicting a method of determining continuous GOR in an oil field. Initially, a set of NMR data is obtained from inside of the wellbore relating to a portion of the subterranean formation (Step 1510). For example, the NMR data may be obtained using the NMR logging system of FIGS. 5 and 6. Quantitative reservoir fluid information, for example the volumetric breakdown and/or the gas saturation of oil, may then be isolated from OBM using radial profiling techniques (e.g., as depicted in FIG. 13 above) based on the set of NMR data (Step 1520). Subsequently, the GOR or other GOR related information may then be determined from the quantitative reservoir information (e.g., gas saturation) based on a predetermined model (e.g., the empirical equation described with respect to FIGS. 11 and 12 above) (Step 1530). The GOR or GOR related information may be generated in a continuous fashion, for example using the NMR logging system of FIGS. 5 and 6 (Step 1540). Based on the quantitative reservoir fluid information, one or more suitable sample acquisition locations may be identified for gathering formation fluid sample to conduct other sample-based measurements (Step 1550). Optionally, such sample measurement results may be used to calibrate the predetermined model, for example to fine-tune the constants in the empirical equation of FIGS. 11 and 12 above.

The steps of portions or all of the processes discussed above may be repeated as desired. Repeated steps may be selectively performed until satisfactory results achieved. For example, steps may be repeated after adjustments are made. This may be done to update the predetermined model and/or to determine the impact of changes made.

Figure 16:
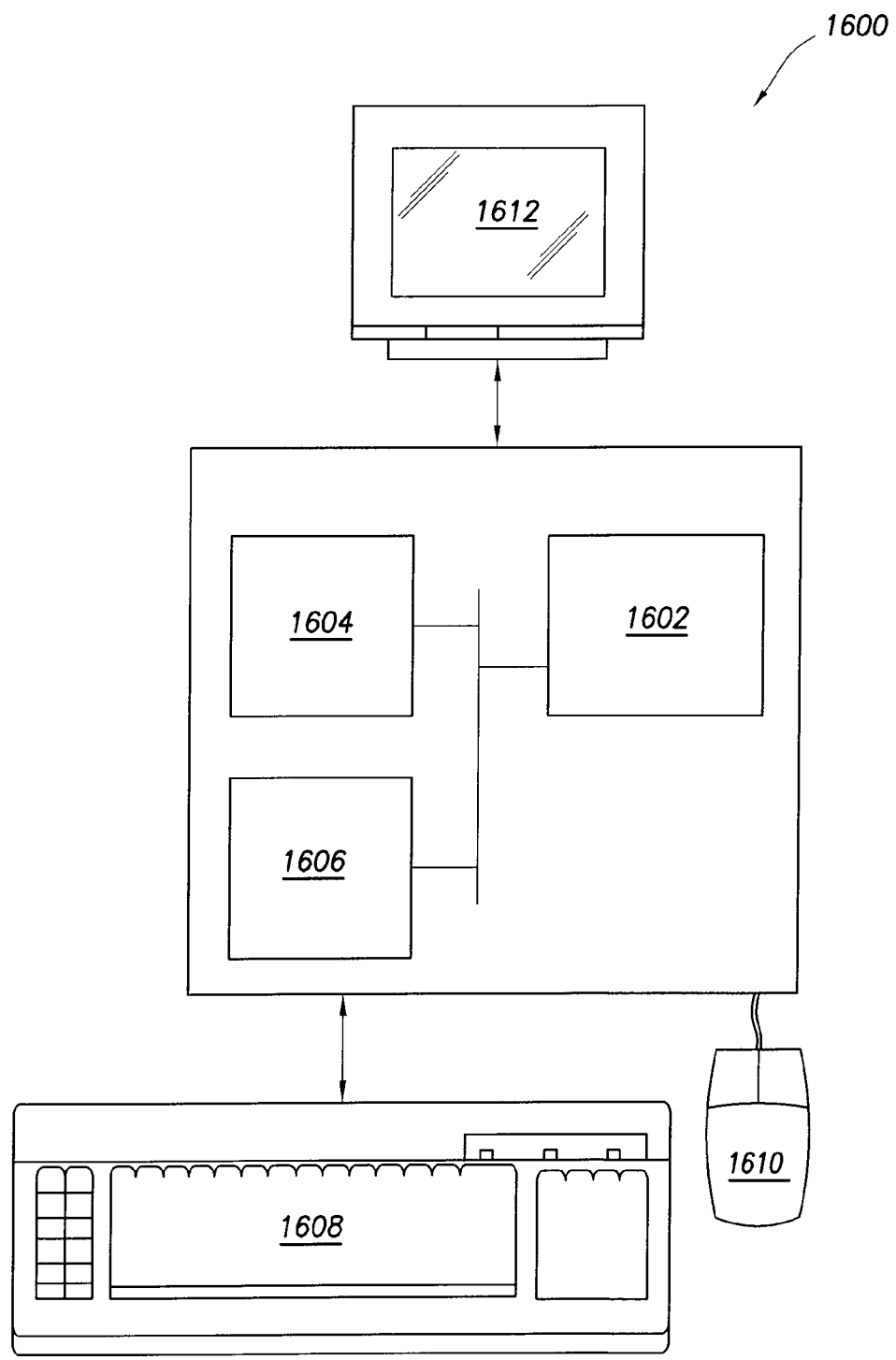
FIG. 16 depicts a computer system in accordance with one or more embodiments of the invention.

The invention may be implemented on virtually any type of computer regardless of the platform being used. For example, as shown in FIG. 16, a computer system (1600) includes one or more processor(s) (1602), associated memory (1604) (e.g., random access memory (RAM), cache memory, flash memory, etc.), a storage device (1606) (e.g., a hard disk, an optical drive such as a compact disk drive or digital video disk (DVD) drive, a flash memory stick, etc.), and numerous other elements and functionalities typical of today's computers (not shown). The computer (1600) may also include input means, such as a keyboard (1608), a mouse (1610) or a microphone (not shown), and output means, such as a monitor (1612) (e.g., a liquid crystal display (LCD), a plasma display, or cathode ray tube (CRT) monitor). The computer system (1600) may be connected to a local area network (LAN) or a wide area network (e.g., the Internet) (not shown) via a network interface connection (not shown). Those skilled in the art will appreciate that these input and output means may take other forms.

Further, those skilled in the art will appreciate that one or more elements of the aforementioned computer system (1600) may be located at a remote location and connected to the other elements over a network. Further, the invention may be implemented on a distributed system having a plurality of nodes, where each portion of the invention (e.g., community system, data source, data provider, software application provider, trust structure, etc.) may be located on a different node within the distributed system. In one embodiment of the invention, the node corresponds to a computer system. Alternatively, the node may correspond to a processor with associated physical memory. The node may alternatively correspond to a processor with shared memory and/or resources. Further, software instructions to perform embodiments of the invention may be stored on a computer readable medium such as a compact disc (CD), a diskette, a tape, a file, or any other computer readable storage device.

It will be understood from the foregoing description that various modifications and changes may be made in the preferred and alternative embodiments of the present invention without departing from its true spirit. For example, the simulators, couplings and arrangement of the system may be selected to achieve the desired simulation. The simulations may be repeated according to the various configurations, and the results compared and/or analyzed.

This description is intended for purposes of illustration only and should not be construed in a limiting sense. The scope of this invention should be determined only by the language of the claims that follow. The term "comprising" within the claims is intended to mean "including at least" such that the recited listing of elements in a claim are an open group. "A," "an" and other singular terms are intended to include the plural forms thereof unless specifically excluded.

What is claimed is:

1. A method of performing operations for an oilfield having at least one wellsite with a wellbore penetrating a subterranean formation for extracting fluid from an underground reservoir therein, comprising:
    obtaining a set of Nuclear Magnetic Resonance (NMR) data of a portion of the subterranean formation from inside the wellbore without acquiring formation fluid sample;
    isolating a quantitative reservoir fluid information associated with oil from oil based mud (OBM) using radial profiling of the set of NMR data, wherein the OBM is used for extracting fluid from the underground reservoir;
    determining gas-oil-ratio (GOR) related information associated with the portion of the subterranean formation from the quantitative reservoir fluid information associated with oil, wherein the GOR related information is determined based on a predetermined model; and
    performing operations for the oilfield based on the GOR related information.

2. The method of claim 1, wherein the predetermined model is established based on a non-NMR measurement.

3. The method of claim 1, further comprising:
    identifying a sample acquisition location for a sample-based measurement inside the wellbore based on the quantitative reservoir fluid information, wherein the sample-based measurement comprises at least one selected from a group consisting of resistivity measurement, viscosity measurement, and optical index measurement.

4. The method of claim 3, further comprising:
    performing the sample-based measurement of a sample acquired at the sample acquisition location to generate a sample measurement result; and
    adjusting the predetermined model based on the sample measurement result.

5. The method of claim 1, further comprising:
    performing a continuous NMR scan through at least a portion of the wellbore; and
    generating a continuous log of GOR related information.

6. A system for performing operations for an oilfield having at least one wellsite with a wellbore penetrating a subterranean formation for extracting fluid from an underground reservoir therein, comprising:
    a downhole tool configured to move in the wellbore;
    a Nuclear Magnetic Resonance (NMR) module disposed in the downhole tool for obtaining a set of NMR data of a portion of the subterranean formation from inside the wellbore without acquiring formation fluid sample;
    a processor; and
    memory comprising instructions when executed by the processor having functionalities to:
        isolate a quantitative reservoir fluid information associated with oil from OBM using radial profiling of the set of NMR data, wherein the OBM is used for extracting fluid from the underground reservoir; and
        determine GOR related information associated with the portion of the subterranean formation from the quantitative reservoir fluid information associated with oil, wherein the GOR related information is determined based on a predetermined model,
    wherein operations for the oilfield is performed based on the GOR related information.

7. The system of claim 6, wherein the predetermined model is established based on a sample-based measurement.

8. The system of claim 6,
    wherein a sample acquisition location is determined inside the wellbore for a sample-based measurement, wherein the sample-based measurement comprises at least one selected from a group consisting of resistivity measurement, viscosity measurement, and optical index measurement.

9. The system of claim 8,
    wherein the sample-based measurement of a sample acquired at the sample acquisition location is performed to generate a sample measurement result; and
    wherein the predetermined model is adjusted based on the sample measurement result.

10. The system of claim 6, wherein the instructions when executed by the processor having further functionalities to:
    perform a continuous NMR scan through at least a portion of the wellbore; and
    generate a continuous log of GOR related information.

11. A computer readable medium comprising instructions executable by a processor to perform a method, the method comprising:
    obtaining a set of Nuclear Magnetic Resonance (NMR) data of a portion of the subterranean formation from inside the wellbore without acquiring formation fluid sample;
    isolating a quantitative reservoir fluid information associated with oil from oil based mud (OBM) using radial profiling of the set of NMR data, wherein the OBM is used for extracting fluid from the underground reservoir;
    determining gas-oil-ratio (GOR) related information associated with the portion of the subterranean formation from the quantitative reservoir fluid information associated with oil, wherein the GOR related information is determined based on a predetermined model; and performing operations for the oilfield based on the GOR related information.

12. The method of claim 11, wherein the predetermined model is established based on a non-NMR measurement.

13. The method of claim 11, further comprising:
identifying a sample acquisition location for a sample-based measurement inside the wellbore based on the quantitative reservoir fluid information, wherein the sample-based measurement comprises at least one selected from a group consisting of resistivity measurement, viscosity measurement, and optical index measurement.

14. The method of claim 13, further comprising:
performing the sample-based measurement of a sample acquired at the sample acquisition location to generate a sample measurement result; and
adjusting the predetermined model based on the sample measurement result.

15. The method of claim 11, further comprising:
performing a continuous NMR scan through at least a portion of the wellbore; and
generating a continuous log of GOR related information.

* * * * *